United States Patent [19]

Veech

[11] Patent Number: 4,649,050

[45] Date of Patent: Mar. 10, 1987

[54] ELECTROLYTE SOLUTIONS CONTAINING POLYANIONIC MATERIALS

[76] Inventor: Richard L. Veech, 712 Brent Rd., Rockville, Md. 20850

[21] Appl. No.: 747,858

[22] Filed: Jun. 24, 1985

Related U.S. Application Data

[63] Continuation of Ser. No. 623,101, Jun. 22, 1984, abandoned.

[51] Int. Cl.$^4$ .............................................. A61K 33/14
[52] U.S. Cl. .................................... 424/153; 424/127; 514/2
[58] Field of Search ............................... 424/127, 153

[56] References Cited

U.S. PATENT DOCUMENTS

| 4,308,255 | 12/1981 | Raj et al. | 424/127 |
|---|---|---|---|
| 4,439,424 | 3/1984 | Ecanow et al. | 424/127 |
| 4,489,535 | 12/1984 | Veltman | 424/153 |

FOREIGN PATENT DOCUMENTS

| WO86/239 | 1/1986 | PCT Int'l Appl. |
| WO86/227 | 1/1986 | PCT Int'l Appl. |
| WO86/228 | 1/1986 | PCT Int'l Appl. |
| WO86/335 | 1/1986 | PCT Int'l Appl. |

OTHER PUBLICATIONS

Latta, T. (1832) Malignant Cholera. Documents . . . Relative to the Treatment of Cholera by Copious Injection of Aqueous & Saline Fluids into the Veins. *Lancet* ii; 272–277.
Ringer, S. (1883) A Further Contribution Regarding the Influence of the Different Constituents of the Blood on the Contraction of the Heart, *J. Physiol* 4: 29–42.
Hartman, A. F. (1934) Theory & Practice of Parenteral Fluid Administration, *JAMA* 103: 1349–1354.
Locke, F. S. (1900) Die wirkung der metalle des blutplasma & verschiedener zucker auf das isolirte saugerthierherz, *Zentrablatt fuer Physiologie* 14: 670–673.
Tyrode, M. N. (1910) The Mode of Action of Some Purgative Salts, *Arch int. Pharmacedyn* 20: 205–223.
Krebs, H. A., Henseleit K. (1932) Untersuchugen uber die Hernstoffbildung im tierkorper. *Hoppe-Seyler's Z Physiol Chem* 210: 33–66.
Krebs, H. A. (1950) Body Size & Tissue Respiration. *Biochem Biophys Acta* 4: 249–269.
Dawson, A. M. C., Elliott, D., Elliot, W. H., Jone, K. M. (1969) Data for Biochemical Research 2nd ed., Clarendon Press, Oxford, p. 507 "Physiological Media".
Fox, Ch., Winfield, J. M., Slobody, L. B., Swindler, C. M., Lattimer, J. K. (1952) Electrolyte Solution Approximating Plasma Concentrations with Increased Potassium for Routine Fluid & Electrolyte Replacement. *JAMA* 148, 827–833.
Mion, C. M., Hegstrom, R. M., Boen, S. T., Scribner, B. H. (1964) Substitution of Sodium Acetate for Sodium Bicarbonate in the Bath for Hemodialysis, *Trans Amer Soc Artif Int. Organs* 10: 110–113.
Parsons, F. M., Stewart, W. K. (1983) The Composition of Dialysis Fluid. In: Replacement of Renal Function by Dialysis, 2nd ed., (Drukker, W., Parsons, F. M., Maher, J. F., eds.) Martinus Nijhoff, Highan, pp. 148–170.
*Facts and Comparisons*, Oct. 1981–Aug. 1983, J. B. Lippincott: St. Louis, 35d–53.
*Documenta Geigy Scientific Tables* (1962 Essellier, A. F., Jeanneret, P., Aqueous Solutions–Parenteral Infusion Therapy. pp. 331–334, Geigy Pharmaceutical Co. Ltd., Manchester.
Merck Manual 12th ed. (1972) Electrolytic, Caloric and Water Balance Agents. pp. 1866–1867.
Veech, R. L., Eggleston, L. V., Krebs, H. A. (1969) The Redox State of Free Nicotin Amide–Adenine Dinucleotide Phosphate in the Cytoplasm of Rat Liver, *Biochem J* 115, 609–619.
Veech, R. L., Lawson, J. W. R., Cornell, N. W., Krebs, H. S. (1979) Cytosolic Phosphorylation Potential, *J. Biol Chem* 254: 6538–6547.
Veech, R. L., Cook, G. A., King, M. T. (1980) Relationship of Free Cytoplasmic Pyrophosphate to Liver Glucose Content & Total Pyrophosphate to Cytoplasmic Phosphorylation Potential, *FEBS Lett* 117: K65–K72.
Sistare, F. D., Haynes, R. C., Jr., (1985) The Interaction Between the Cytosolic Pyridine Mucleotide Redox Potential & Gluconeogenisis from Lactate/Pyruvate in Isolated Rat Hepatocytes. *J Biol Chem* 260, 12748–12753.
Sistare, F. D., Haynes, R. C., Jr., (1985) Acute Stimulation by Gluconeogenisis from Lactate/Pyruvate in Isolated Hepatocytes from Normal and Adrenolectonized Rats. *J Biol Chem* 260: 1254–12760.
Veech, R. L. (1966) The Toxic Impact of Parenteral Fluid Therapy *J Clin Nutr* (in press).
Tanford, C. S. (1950) *J Am Chem Soc* 72: 441–451 Preparation & Properties of Serum Plasma Proteins. XXIII. Hydrogen Ion Equilibria in Nature & Modified Human Serum Albumin.
C. Tanford, J. Am. Chem. Soc. 42: 441–451, 1950.

*Primary Examiner*—Sam Rosen
*Attorney, Agent, or Firm*—Hill, Van Santen, Steadman & Simpson

[57] ABSTRACT

The use of non diffusible organic polyionic materials in aqueous electrolyte solutions is taught wherein the electrolyte types and concentrations are suitable for use in treating living animal cells (including mammals and man). In these solutions, the Na:Cl ratio is normalizable without the use of unphysiological or demonstrably pathological amounts or ratios of small diffusible anions. Effective plasma expanders and plasma substitutes are provided. Near equilibrium couples may be incorporated if desired.

12 Claims, No Drawings

ELECTROLYTE SOLUTIONS CONTAINING POLYANIONIC MATERIALS

RELATED APPLICATION

This application is continuation of my parent application identified by U.S. Ser. No. 623,101, filed June 22, 1984, now abandoned.

BACKGROUND OF THE INVENTION

1. Field of the Invention

This invention lies in the field of electrolyte fluids and processes for their preparation and use.

2. State of the Art

Fluids designed to contact mammalian cells all have as a general characteristic an osmotic pressure above about 260 milliosmoles/liter (mOs/L). The most common fluid given is 5% dextrose in $H_2O$. The second most common fluid given is normal saline (0.9N or 0.095% NaCl). It has been known (Black DAK, *Lancet* i: 305–312, 1954) that giving to adult humans much over 500 ml of normal saline per day leads to hyperchloremic acidosis since normal plasma contains about 136–145 mEq/L (milliequivalents per liter) plasma $Na^+$ and about 100–106 mEq/L plasma of $Cl^-$ for an average Na:Cl milliequivalent ratio of about 1:36. There has been a long standing interest in creating an artificial plasma which dates back to 1883 with the origin of S. Ringer's solutions (*J Physiol* 4: 29–42, 1883) which are still in use today. It is now recognized that plasma is an "unmakable" solution since the law of electrical neutrality requires that the number of positive ions (cations) equal the number of negative ions (anions). Plasma itself has an exceedingly complex composition.

As any practicing clinician knows, since plasma contains 25–28 mEq/L of $HCO_3^-$, the number of measurable (+) cations in plasma is greater than the number of measurable (−) anions (mainly $Cl^-$, $HCO_3^-$, and small amounts of $P_i^{-1.8}$) in plasma by about 10–17 mEq/L plasma. The difference between cations and anions is called the apparent "anion gap". Efforts to cure the anion gap have been attempted since about the time of Ringer. A similar gap exists in each of extracellular and intracellular fluids.

The anion gap is now known to be caused mainly by the presence of polyanionic proteins, especially albumin which in man and mammals generally is a protein of about 68,000 M.W. (molecular weight) and which has about 20 negative (anion) charges/mole at the physiological pH of blood which is about 7.35 to 7.45 (see Tanford C. *J Am Chem Soc* 42: 441–451, 1950). Since the normal albumin concentration in, for example, mammalian blood is about 0.65 mM/L (millimoles per liter), about 13 mEq/L of the plasma anion gap is due to this source. Although albumin is found in all mammalian plasma, its chemical structure differs from species to species. If albumin from an animal such as the cow is intravenously introduced into man, an allergenic response promptly results. Therefore, only albumin specific to a species may be used repeatedly in a therapeutic situation. Although (suitably purified) albumin from one human can be so introduced into another without an allergenic response, human albumin is costly, a potential source of infection with viral agents, such as hepatitis or AIDS, and is difficult to obtain in quantity at the present time, as for therapeutic purposes. Thus, electrolyte solutions for therapeutic use which do not require use of a material such as albumin are still useful.

The history of electrolyte solutions including dialysis media can be briefly related:

(1) Sodium chloride. The earliest solutions used in medical therapy (Latta T. *Lancet* i: 274–277, 1832) contained sodium cations ($Na^+$) and chloride anions ($Cl^-$). Today, normal saline, which is isomolar NaCl (0.9–0.95%) is still given to patients intravenously. The problems with such solution are that it does not regulate pH and it induces hyperchloremic acidosis when given at much over 1 L/70 kg man/day.

(2) Ringer's. The second attempt to make a fluid which was not immediately lethal for contacting human cells was designed by S. Ringer in the 1880's and is still in use today. This fluid composition is essentially 130–145 mEq/L $Na^+$, 2–4 mEq/L $K_+$, 3.00 mEq/L $Ca^{2+}$, 100–134 mEq/L $Cl^-$, 7–14 mEq/L $P_i^{-1.8}$, and optionally up to 30–45 mEq/dl-Lactate or acetate, when a normal Na:Cl ratio is to be obtained.

Ringer's lactate is now known to cause profound difficulties with the cellular redox state (see equation 4) and has poor buffering capacity. This led in the 1920's and 30's to development of a series of physiologically compatible fluids designed by the great names of modern biology: Warburg, Locke, and Tyrode, and culminated in 1932 with the development of Krebs-Henseleit solution.

(3) Krebs-Henseleit. (Krebs HA, Henseleit KA. *Hoppe-Seyler's Z Physiol Chem* 210: 33–66, 1932) Krebs-Henseleit solution has a composition as given in Table 2 herein, the essential advance being that it normalizes the $HCO_3^-/CO_2$ ratio, thus achieving adequate pH control. The value of this fluid is attested to by the fact that from it, or its partner, the Krebs Phosphate-Ringers (Krebs HA. *Hoppe-Seyler's Z Physiol Chem* 217: 193 1933), have evolved all the first modern renal dialysis fluids, and many special fluids for tissue perfusion or incubation.

The problem with Krebs-Henseleit solution, aside from too high $Ca_2^+$ (See Burritt MF, Pierides AM, Offord KP *Mayo Clin Proc* 55: 606–613, 1980) and $Mg_2^+$ by factors of about 2, and $SO_4^{2-}$ by even more, is that the remaining anion gap was made up by Krebs with $Cl^-$. Thus again, normal $Cl^-$ is 100–106 mEq/L in plasma, but Krebs-Henseleit contains 127.8 mEq/L. Krebs realized this deficiency and attempted (Krebs HA. *Biochem Biophys Acta* 4: 249–269.1950) to remedy this problem with the creation of Krebs Serum substitute (see Table 2). Because he failed to understand from a theoretical point of view how such a problem could be solved, he picked anions on the basis of $O_2$ consumption measurement in tissue slices. The anions picked to make up the 13 mEq/L anion gap were glutamate$^-$, fumarate$^{2-}$, and pyruvate$^-$, which are inappropriate in living cells (although not in tissue slices where cut surfaces of cells are exposed) because glutamate$^-$ and fumarate$^-$ cannot readily penetrate the cell membrane.

This was really how matters stood until the development of widespread renal dialysis in the 1960's. The pioneering of these life saving techniques largely by Scribner in Seattle, Scribner in Washington, and Merrill and his group at Harvard led to the need for a cheap, convenient fluid. Krebs-Henseleit solution (with only very slight variations, see Table 2) was used by the Harvard group in open baths where the necessary $CO_2$ was lost to the atmosphere with a resultant rise in pH (see equation 1) and the conversion of $HCO_3^-$ to $CO_3{}^{2-}$ salts. This simple problem was inconvenient to the physicians in charge and led them, well-meaning but misguidedly, to seek a more convenient substitute for Krebs-Henseleit solution.

(4) Gilman-Mudge-Scribner and the Substitution of Acetate for $HCO_3$ in High-Volume Fluids. Alfred Gilman of Columbia University was, in effect, the dean of American pharmacologists, and he and his students in the middle 1940's reasoned that acetate is ultimately metabolized to $CO_2$, and since it readily penetrated cell walls, it could be used as an alternative source of $HCO_3{}^-$ (Mudge G H, Manning J A, Gilman A. *Proc Soc Exptl Biol Med* 71: 136-138, 1949). While all of this is true, it ignores the profound upsets in mineral and energy metabolism which, at the time, no one recognized, but which are now clear and which have led to the present invention, since it is now absolutely clear that acetate containing fluids causes profound toxicity which can easily be overcome and therefore can no longer be tolerated in view of the new art described here.

About 80% of all current hemodialysis fluids in the U. K. use 35 mM/l acetate$^-$ in combination with 130-150 mM Na$^+$, 1-1.75/mmole $Ca^{2+}$, 0-1mM/L $Mg^{2+}$, and 100/mM/L Cl$^-$ (See Parsons F M, Stewart W K In: Drukker W, Parsons F M, Maher J F, eds. *Replacement of Renal Function by dialysis.* 2nd Edition, 1984, Martinus Nijhoff: Hingham, pp 148-170). Minor alterations in commercial fluids involve the use of d,l-lactate (35-50 mM/L) in place of acetate, but this alternative from commercial sources is almost as unsatisfactory as acetate and is submitted to be no longer tolerable for patient care.

Prior art illustrative of electrolyte solutions are provided in Tables I, II, and III herewith.

TABLE I

| | | Prior Art Fluids to Which Macromolecules Have Been Added | | | | | |
|---|---|---|---|---|---|---|---|
| Units mmoles | Normal Plasma N.E.J.M. 283, 1285 | (1) 5% Dextrose in Water | (2) Normal Saline 0.9% | (3) Ringer's Injectable | (4) Lactated Ringer's | (5) Acetated Ringer's | (6) Range of Peritoneal Dialysis |
| L fluid | 1970 | | | | | | (Commercial) |
| Na | 136-145 | | 154 | 147 | 130 | 140 | 131-141.5 |
| K | 3.5-5.0 | | | 4 | 4 | 10 | 0-4 |
| Ca | 2.1-2.6 | | | 2.5 | 1.5 | 2.5 | 1.75-2.0 |
| free [Ca2+] | [1.06] | | | | | | |
| Mg | 0.75-1.25 | | | 2.5 | 1.5 | 1.5 | 0.25-0.75 |
| free [Mg2+] | [0.53] | | | | | | |
| Σ mEq Cations | 142.7-153.2 | | 154 | 156 | 137 | 158 | 135-151 |
| Cl | 100-106 | | 154 | 156 | 109 | 103 | 96-106 |
| $HCO_3$ | 26-28 | | | | | | |
| Σ Pi | 1-1.45 | | | | | | |
| $SO_4$ | 0.32-0.94 | | | | | | |
| L-lactate | 0.6-1.8 | | | | 28(d,l) | 8(d,l) | 35-45(d,l) |
| pyruvate | | | | | | | |
| Lact/pyr | | | | | * | * | * |
| D-β-OHbutyrate | | | | | | | |
| acetoacetate | | | | | | | |
| β-HB/ acac | | | | | | | |
| acetate | | | | | | 47 | 45 |
| Other | | | | | | | |
| ΣmEq anions | 128.7-139.4 | | 154 | 156 | 137 | 158 | 135-151 |
| Na/Cl | 1.28-1.45 | | 1.00 | 0.94 | 1.19 | 1.36 | 1.36-1.33 |
| Glucose | 3.9-5.6 | 278 | | | | | 83-236 |
| or others | | | | | | | |
| $CO_2$ | 0.99-1.39 | | | | | | |
| pH | 7.35-7.45 | ≈5.5-6.5 | ≈5.5-6.5 | ≈6.0-6.5 | ≈6.0-6.5 | ≈6.0-6.5 | ≈6.0-6.5 |
| Σ mOsm | 285-295 | 278 | 310 | 309 | 272 | 312 | 347-535 |
| Use: | | Hydration & Nutrition | NaCl Replacement | Multiple | IV Fluid Blood Products Administration | Electrolyte Replacement | Peritoneal Dialysis |

(1) Facts and Comparisons Lippincott, St Louis, 1981
(2) Facts and Comparisons Lippincott, St Louis, 1981
(3) Facts and Comparisons pp 35d-53, Oct '81-Aug '83, JB Lippincott, St Louis. Ringer S. J Physiol 4: 29-42, 1883.
(4) Facts and Comparisons pp 35d-53, Oct '81-Aug '83, JB Lippincott, St Louis. Hartmann AF. J Am Med Assoc 103: 1349-1354. 1934.
(5) Facts and Comparisons pp 35d-53, Oct '81-Aug '83, JB Lippincott, St Louis. Fox CL, Winfield JM, Slobody LB, Swindler CM, Lattimer JK. J Am Med Assoc 148: 827-833, 1952.
(6) Facts and Comparisons pp 35d-53, Oct '81-Aug '83, JB Lippincott, St Louis.

TABLE II

| | | Fluids to Which Complex Macromolecules Are Added | | | | | |
|---|---|---|---|---|---|---|---|
| Units mmoles | Normal Plasma N.E.J.M. 283, 1285 | (8) Hypertonic NaCl (Resusitation) | (9) Tyrode's | (10) Krebs Henseleit | (11) Brigham Dialysis | (12) Scribner's Dialysis | (13) Range of Acetate Hemodialysis |
| L fluid | 1970 | | | | | | |
| Na | 136-145 | 1200 | 150.1 | 143 | 140 | 135 | 130-145 |
| K | 3.5-5.0 | | 5.9 | 5.9 | 4 | 1.5 | 0-5 |
| Ca | 2.1-2.6 | | 1.8 | 2.5 | 1.25 | 1.25 | 1.25-2.0 |
| free [Ca2+] | [1.06] | | | | | | |
| Mg | 0.75-1.25 | | 0.45 | 1.2 | 0.5 | 0.5 | 0-1 |

TABLE II-continued

Fluids to Which Complex Macromolecules Are Added

| Units mmoles | Normal Plasma N.E.J.M. 283, 1285 | (8) Hypertonic NaCl (Resusitation) | (9) Tyrode's | (10) Krebs Henseleit | (11) Brigham Dialysis | (12) Scribner's Dialysis | (13) Range of Acetate Hemodialysis |
|---|---|---|---|---|---|---|---|
| free [Mg2+] | [0.53] | | | | | | |
| ΣmEq Cations | 142.7–153.2 | 1200 | 160.5 | 156.3 | 147.5 | 140 | 138–147 |
| Cl | 100–106 | 1200 | 147.48 | 127.8 | 120.7 | 105 | 92–111 |
| HCO$_3$ | 26–28 | | 11.9 | 25 | 26.8 | | |
| Σ Pi | 1–1.45 | | 1.22 | 1.18 | | | |
| SO$_4$ | 0.32–0.94 | | | 1.18 | | | |
| L-lactate | 0.6–1.8 | | | | | | |
| pyruvate | | | | | | | |
| Lact/pyr | | | | | | | |
| D-β-OHbutyrate | | | | | | | |
| acetoacetate | | | | | | | |
| β-HB/ acac | | | | | | | |
| acetate | | | | | | 35 | 35–45 |
| Other | | | | | | | |
| ΣmEq anions | 128.7–139.4 | 1200 | 161.6 | 157.3 | 147.5 | 140 | 138–147 |
| Na/Cl | 1.28–1.45 | 1.00 | 0.96 | 1.12 | 1.16 | 1.29 | 1.29–1.31 |
| Glucose | 3.9–5.6 | | 5.6 | | 10 | | |
| or others | | | | | | | |
| CO$_2$ | 0.99–1.39 | — | | 1.24 | 1.24 | | |
| pH | 7.35–7.45 | ≈5.5–6.5 | 7.1 | 7.4 | 7.4 | ≈5.5–6.5 | ≈5.5–6.5 |
| Σ mOsm | 285–295 | 2400 | 318.8 | 308 | 304.8 | 278.2 | 258–309 |
| Use: | | Hemorrhage & Shock | Perfusion | General | Hemodialysis | Hemodialysis | Hemodialysis |

(8) Velasco IT, Pontieri V, Rocha M, Silva E, Lopes OU. Am J Physiol 239: H664–673, 1980. Hypertonic Ringer's Lactate has also been advocated in treatment of hemorrhage. See Nerlich M, Gunther R, Demling RH. Circ Shock 10:179–188, 1983. Both are inadequate.
(9) Tyrode MJ. Arch int Pharmacodyn 20: 205, 1910.
(10) Krebs HA, Henseleit KA. Hoppe-Seyler's Z Physiol Chem 210: 33–66, 1932.
(11) Murphy WP, Swan RC, Walter C, Weller JM, Merrill JP. J Lab Clin Med 40: 436–445, 1952.
(12) Mion CM, Hegstrom RM, Boen ST, Scribner BH. Trans Am Soc Artif Intern Organs 10: 110–113, 1964. The use of acetate in physiological fluids was first proposed by: Mudge GH, Manning JA, Gilman A. Proc Soc Exptl Biol Med 71: 136–138, 1949.
(13) Parsons FM, Stewart WK. In: Replacement of Renal Function by Dialysis (Drukker W, Parsons FM, Maher JF, eds) 2nd Edition, Martinus Nijhoff, Hingham, pp 148–170.

TABLE III

"Prior Art" Fluids To Which Macromolecules Have Been Added

| Units mmoles | Normal Plasma N.E.J.M. 283, 1285 | (15) Krebs Liver Perfusion with Bovine serum Albumin and Red Cells | (16) Schimassek Liver Perfusion | (17) Krebs Kidney Perfusion | (18) Hepatocyte Incubation | (19) Bahlman Kidney Perfusion | (20) Fulgraff Kidney Perfusion |
|---|---|---|---|---|---|---|---|
| L fluid | 1970 | | | | | | |
| Na | 136–145 | 153 | 151.54 | 148 | 153 | 147 | 143 |
| K | 3.5–5.0 | 5.9 | 5.9 | 5.9 | 5.9 | 4.9 | 4.74 |
| Ca | 2.1–2.6 | 2.5 | 1.8 | 2.5 | 2.5 | 2.56 | 1.25 |
| free [Ca2+] | [1.06] | | | | | | |
| Mg | 0.75–1.25 | 1.2 | 0.49 | 1.2 | 1.2 | 1.2 | 0.59 |
| free [Mg2+] | [0.53] | | | | | | |
| ΣmEq Cations | 142.7–153.2 | 166.3 | 162.02 | 161.3 | 166.3 | 159.4 | 151.15 |
| Cl | 100–106 | 127.8 | 147.48 | 127.8 | 127.8 | 127 | 113.04 |
| HCO$_3$ | 26–28 | 25 | 11.9 | 25 | 25 | 24.5 | 25 |
| Σ Pi | 1–1.45 | 1.18 | 1.22 | 1.18 | 1.18 | 1.18 | 1.18 |
| SO$_4$ | 0.32–0.94 | 1.18 | — | 1.2 | 1.2 | 1.18 | 1.18 |
| L-lactate | 0.6–1.8 | (10 Na-1 Lac) | 1.33 | 5 Na 1-Lac | 9.09 | 2.75(d,1) | 3.5(?d,1) |
| pyruvate | | | 0.09* | | 0.91 | 0.25 | 0.25 |
| Lact/pyr | | | 14.8 | | 10 | 10 | 7 or 14 |
| D-β-OHbutyrate | | | | | | | |
| acetoacetate | | | | | | | |
| β-HB/ acac | | | | | | | |
| acetate | | | | | | | 5.0 |
| Other | | | | | | | |
| ΣmEq anions | 128.7–139.4 | 167.0 | 162.81 | 162.3 | 167.0 | 159.1 | 151.31 |
| Na/Cl | 1.28–1.45 | 1.12 (1.20) | 1.03 | 1.16 | 1.20 | 1.20 | 1.26 |
| Glucose | 3.9–5.6 | | 5.45 | | | 6.2 | — |
| or others | | | | | | 6.7 urea | 6.7 urea |
| CO$_2$ | 0.99–1.39 | 1.25 | 1.24 | 1.24 | 1.24 | 1.24 | 1.24 |
| pH | 7.35–7.45 | 7.4 | 7.1 | 7.4 | 7.4 | 7.4 | 7.4 |
| Σ mOsm | 285–295 | 328 | 321 | 318 | 328 | 327 | 307.9 |

TABLE III-continued

"Prior Art" Fluids To Which Macromolecules Have Been Added

| Units mmoles | Normal Plasma N.E.J.M. 283, 1285 | (15) Krebs Liver Perfusion with Bovine serum Albumin and Red Cells | (16) Schimassek Liver Perfusion | (17) Krebs Kidney Perfusion | (18) Hepatocyte Incubation | (19) Bahlman Kidney Perfusion | (20) Fulgraff Kidney Perfusion |
|---|---|---|---|---|---|---|---|
| Albumin (g %) | 3.5–5 | 3.9 | 2.5 | 5 | 2.5 | 5.5 | 0.05 |

*Artificial perfusion fluid generally add 1.5 to 8 g % albumin, dialyzed against a medium listed in Table I; that is Krebs-Henseleit (10), Krebs-Ringer Phosphate (11), Tyrode's (9), Locke's (8), or Krebs-Henseleit with a lowered Ca$^{2+}$ to the 1 mM range, particularly in heart perfusion. They may or may not contain red cells. Krebs-Henseleit is known to contain about twice the amount of ionized CA$^{2+}$ as serum.
(15) Hems R, Ross BD, Berry MN, Krebs HA. Biochem J 101, 284, 1966; Krebs Henseleit (10) with 3.9 g % bovine albumin.
(16) Schmassek J. Biochem Z 336, 460, 1963. Essentially Tyrode's (9) with added lactate and pyruvate.
(17) Nishiitsutsuji-Uwo JM, Ross BD, Krebs HA. Biochem J 103, 852–862, 1967; Krebs-Henseleit (10) with 5 g % albumin, dry.
(18) Crow KE, Cornell NW, Veech RL. Biochem J 172, 29–36, 1978, Krebs-Henseleit (10) with 2.5 g % dialysed albumin plus l-lactate plus pyruvate.
(19) Bahlman J et al. Am J Physiol 212, 77 1967; Krebs Henseleilt (10) with lactate and pyruvate and 5.5 g % bovine albumin
(20) Fulgraff et al. Arch int Pharmacodyn 172, 49, 1972; Krebs-Henseleit (10) with ½ Mg and Ca plus lactate and pyruvate plus 5 mM acetate, plus 0.05 g % albumin plus 2 g % albumin plus 2 g % hemocel.

Prior art electrolyte solutions which incorporated albumin are illustrated in Table III herewith. In the prior art solutions, even those containing albumin, the sodium cation to chloride anion milliequivalent ratio was never normalized or made to fall in a range associated with normal animal cells in a manner which would not induce measureable toxic effects in the cells so contacted (or with the particular animal fluid which was to be mimicked by a particular fluid, for example, human blood plasma compared to Krebs-Henseleit solution).

So far as now known, the only organic polyanionic substance heretofore employed in aqueous electrolyte solutions has been albumin, "hemocel" or gelatin and no such electrolyte solution is believed to have either a Na:Cl milliequivalent ratio in the physiologically normal range or an electrolyte composition comparable to normal mammalian (or human) blood plasma. Furthermore, so far as is now known, no albumin containing such electrolyte solution has ever previously been employed in in vivo mammalian therapy (e.g., parenterally, intravenously, or otherwise administered).

In even the field of plasma expanders (which is regarded as an application for aqueous electrolyte solutions suitable for contacting living animal cells), it has heretofore been thought by those skilled in the art (see, for example, Mudge on "Agents Affecting Volume and Composition of Body Fluids", pp. 848–884 of Goodman & Gilman's, The Pharmacologic Basis of Therapeutics published in 1980 by Macmillan, New York, that an ideal plasma expander should be, among other properties, pharmacologically inert. While many substances have been investigated as plasma expanders, organic polyanionic substances (whether natural or synthetic in origin) do not appear to have previously been considered. Dextran (see Mudge, reference cited) appears to be regarded as the best known artificial plasma expander, yet dextran is a branched polysaccharide of about 200,000 glucose units with a molecular weight of about 40 million and which has no anionic charge.

In my copending U.S. patent applications U.S. Ser. No. 623510, U.S. Ser. No. 623102 and U.S. Ser. No. 623443, identified by attorney's docket numbers P-83,2198, P-83,2213, P-83,1655 and P-85,1402, P-85,1403, P-85,1404 provide aqueous electrolyte fluids which are also useful for contacting living animal cells, but these electrolyte fluids do not, in contrast to the fluids of the present invention, require the use of organic polyionic substances. For present disclosure purposes, the entire disclosure and contents of these copending applications is incorporated herein by reference. Definitions used in such copending applications, for example, are incorporated hereinto by reference.

BRIEF SUMMARY OF THE INVENTION

This invention relates to new and improved aqueous electrolyte solutions suitable for contacting living animal cells and to processes for making and using the same.

The solutions (and processes of use) of this invention are employable in, for example:
1. intravenous electrolyte and fluid therapy for mammals (including man);
2. dialysis fluids (both hemo and peritoneal);
3. parenteral nutrition (when administered in combination with nutrients);
4. perfusion media (with or without nutrients);
5. incubation media (with or without nutrients);
6. tissue culture (usually used with nutrients);
7. plasma expanders and substitutes; and the like.

Aqueous electrolyte solutions of this invention comprise:
(a) at lease one inorganic cation,
(b) at least one inorganic anion, and
(c) optionally at lease one non diffusible polyionic material.

In any given solution, the total positive charges equal the total negative charges. The concentration of any one of such polyionic material is always less than about 10,000 millimoles per liter and the minimum concentration of any one such ionic material is always at least about 0.1 millimoles per liter, and similarly for each of said inorganic cation(s) and said inorganic anion(s).

The charge Z associated with a molecule of any given such polyionic material can vary from greater than zero to infinity.

The molarity (number of moles per liter) of such polyionic material multiplied by Z produces a charge value indicating the total anionic equivalents of a given polyionic material in a given solution. The polyionic material can be anionic, cationic, or even a mixture of such.

One class of the electrolyte solutions of this invention incorporates at least one organic polyanionic substance of predeterminable and variable anionic charge. Such a substance is employed to fill, in whole or in part, the anion gap of a given aqueous electrolyte solution, and thus normalizes the Na:Cl milliequivalent ratio of the resulting solution.

Another class of the electrolyte solutions of this invention incorporates at lease one organic polycationic substance of predeterminable and variable cationic charge. Such a substance is employed to fill, in whole or in part, a cation gap existing in a given aqueous electrolyte solution existing between, for example, inorganic cations and anions in an aqueous electrolyte solution.

For purposes of contacting living cells (e.g. physiological purposes), an organic polyanionic substance useful in the practice of this invention is characterized by having an anionic charge valve which is equal to (molar concentration) times (total anionic charge per molecule) measured at a pH value to be associated with the particular electrolyte solution involved.

Broadly, the pH range of a physiologic solution of this invention can range from about 5 to 9, but physiological pH values in the range from about 6.8 to 7.6 are more preferred, and such pH values in the range from about 7.2 to 7.6 are presently most preferred for in vivo usage and desired physiologic pH. The anionic charge value for an organic polyanionic substance used in such practice of this invention should range from about $-2$ to $-1000$ net milliequivalents/millimole, and preferably from about $-13$ to $-15$ milliequivalents/millimole, and most preferably, about $-14$ milliequivalents/millimole (at a pH of about 7.4).

In general the organic polyionic substances useful in the practice of this invention are characterized by being substantially non diffusible through a semipermeable membrane, such as a semipermeable membrane of the type employed in hemodialysis and substantially impermeant to the mammalian cell membrane by means other than endocytosis.

Particularly when a given organic polyanionic substance is to be used in a physiologic solution that will be employed in mammalian in vivo application(s), it is, of course, preferred that such be:

(1) non-antigenic;
(2) non-pyretic;
(3) metabolizable if taken up by the reticuloendothelial system.

It is more preferred that the metabolizable products produced during enzymatic breakdown of a given organic polyanionic substance constitute safe entry points into the cellular metabolic processes.

For present purposes, the polyionic non diffusible materials used are classifiable into three distinct groups or classes, as follows:

Class I comprised o- naturally occurring proteinaceous substances such as those which occur in blood and blood products;

Class II comprised of polyanionic synthetic polymeric substances such as those which contain pendant acidic groups such as carboxyl, sulfate, sulfonyl, and the like; and Class III comprised of polycationic synthetic polymeric substances such as those which contain pendant basic groups, such as amines and the like.

Examples of Class I substances include serum albumin, washed red cells, and the like. Examples of Class II substances include sodium albuminate carboxymethyl starch, carboxyethyl starch, poly-d-betahydroxybutyrate, carboxymethyl cellulose, cation exchange resins, and the like. Examples of Class III substances include anion exchange resins, and the like.

As used herein, the term ion exchange resin refers to resins that are insoluble solid acids or bases which have the property of exchanging ions from solutions. "Cation exchange resins" contain fixed electronegative (anionic) charges which interact with mobile counterions (cations) having the opposite, or positive, charge. "Anion exchange resins" have fixed electro positive charges and exchange negatively charged anions. Ion exchange resins are three-dimensional macromolecules or insoluble polyelectrolytes having fixed charges distributed uniformly throughout the structure.

Although especially for physiologic in vivo solutions it is presently preferred that the polyanionic material used in the practice of this invention be in a form such that it forms a true solution (presently most preferred), or true stable dispersion in water such that individual units of the material in the aqueous medium are below about 0.01 micron in average particle size, those skilled in the art will appreciate that microscopic particle sizes may be associated with a given polyanionic material when in vitro and other non biochemical applications are contemplated. For example, in the case of using a cation-exchange resin in a dialysis fluid the resin may be in the form of uniform spheres of styrene-divinyl benzene (S-DVB) copolymers having diameters ranging from about 0.3 to 1.0 mm.

In physiologic electrolyte solutions of this invention, especially those intended for in vivo applications indicated, sodium cations and chloride anions are incorporated. The ratio of sodium cation milliequivalents per liter to the chloride anion milliequivalents per liter is within the range found in normal mammalian blood plasma.

The specified milliequivalent ratio of sodium to chloride in normal mammalian blood and in normal animal extracellular fluid and intracellular fluid based on available information is believed to be in the range from about 1.24:1 to 1.47:1. In the case of a normal human adult, this range is now believed to extend (based on published information) from about 1.24:1 to 1.47:1, and preferably from about 1.33:1 to 1.42:1 and most preferably from about 1.36:1 to 1.42:1. These ratios are employed in solutions used in the practices of this invention. However, solutions employed in the practice of this invention can contain a Na:Cl milliequivalent ratio which is somewhat broader than the range considered normal, such as a ratio which is in the range from about 1.24:1 to 1.6:1 depending upon the mammal (or patient), his condition, the purposes of the physician or clinician, and the conditions of treatment.

By the term "milliequivalent ratio" as sometimes used herein, is meant the ratio of milliequivalents per liter of one substance to milliequivalent per liter of another substance in an aqueous medium.

Characteristically, a physiologic solution of this invention contains from about 1 to 2400 millimoles per liter of sodium cations, and more preferably from about 120 to 165 millimoles per liter of sodium cations, and more preferably from about 129 to 163.5 mM/l and most preferably from about 136 to 145 mM/l. In addition, a solution contains sufficient chloride anions to produce the milliequivalent ratio of sodium cations to chloride anions as above defined.

In general, the maximum amount of organic polyanionic material which is used in a physiologic electrolyte solution of this invention is such as to supply an entire anion gap selected for that solution and thereby achieve a particular Na:Cl milliequivalent ratio sought for such solution. The minimum amount of organic polyanionic material which is used in a physiologic electrolyte solution of this invention is such as to make up only a part of the desired anion gap and achieve the desired Na:Cl ratio when more than only the organic polyanionic material is used to help make up such anion gap desired and achieve such desired Na:Cl ratio. As a practical matter, no inherent biochemical minimum effective amount for organic polyanionic material which must be present in a solution of this invention is known or believed to exist. Preferably, however, the minimum total quantity of organic polyanionic material used in any given solution is at least such as to produce a charge value in the range from about 10 to 18 mole charges per liter. The preferred anionic material contains carboxyl groups with a charge density of about 10–30 charges/70,000 MW. Greater density or strength such as $SO_4^{2-}$ groups may cause bleeding abnormalities and can denature protein.

Preferred but optional additives which may be used in combination with organic polyanionic material to close the anion gap and achieve the Na:Cl ratio for a given physiologic solution are described herein below.

Since, as described above, electrolyte solutions of the prior art containing albumin did not contain a normal milliequivalent ratio of Na:Cl, those compositions of the invention which contain albumin and which have such a normalized Na:Cl ratio are submitted to be novel and to constitute a patentable advance in this art since normalization of the Na:Cl ratio avoids acidosis.

Particularly since no prior art electrolyte physiologic solutions are known which contain Class II polyanionic materials as described above, such solutions which contain a normalized Na:Cl ratio are likewise submitted to be novel and to constitute a patentable advance in this art. In addition, however, electrolyte solutions which contain such Class II polyanionic materials and which contain a Na:Cl ratio within the somewhat broader range above characterized are believed to be novel and useful and never previously known to the art since extremes of Na:Cl ratio in combination with Class II polyanionic materials offer new patentably useful fields of use and applications under both in vivo and in vitro use conditions not heretofore possible.

Optionally, in addition to sodium, a solution of this invention can contain one or more of the following additional metallic cations in the respective quantity as indicated below:

| Cation Component | Quantity range (millimoles per liter) | |
| --- | --- | --- |
| | broad | preferred |
| potassium | 0–90 | 0–5 |
| calcium | 0–60 | 0–2.5 |
| magnesium | 0–15 | 0–1 |

Optionally a solution of this invention can have additionally incorporated (dissolved) therein from 0 to about 550 millimoles per liter of at least one substantially nonionic (including zwitterionic) osmotically active substance (which is preferably metabolizable).

Examples of usable such nonionic substances include glucose, glycerol, fructose, sorbitol, and the like. Glucose is presently most preferred.

A physiologic electrolyte solution used in the practice of this invention is further characterized by generally having:

(1) sufficient total substances in the absence of any nonionics dissolved therein to produce an osmolarity ranging from about 260 to 5000 milliosmoles (mOs) and preferably from about 265 to 550 mOs and most preferably from about 280 to 320 in mOs;

(2) the relationship between total ionic substances is such that the pH ranges from about 5 to 9, and preferably from about 6.9 to 8.6; and most preferably from about 7.35 to 7.55;

(3) the charges of all cations equal the charges of all anions; and (4) the minimum total concentration of all such near equilibrium couple(s) present is at least about 0.1 millimoles per liter, and preferably is at least about 0.5 mM/l, and more preferably about 2 mM/l, while the maximum concentration thereof is preferably not more than about 465 mM/L and more preferably is not more than about 61 mM/l and most preferably is not more than about 50 mM/l.

(5) Non-physiological electrolyte solutions of this invention may be made in like manner and may be used to prepare ion exchange resins, active enzyme solutions and the like.

Various additional objects, aims, and purposes, features, advantages, applications, variations, and the like will be apparent to those skilled in the art from the teachings of the present specification taken with the claims.

DETAILED DESCRIPTION

Optional Anion Gap Components

In addition to the organic polyanionic materials in the anion gap of a given electrolyte solution of the present invention one may include in the anion gap at least one near equilibrium couple selected from the group consisting of (1) bicarbonate⁻ and carbon dioxide, (2) l-lactate⁻ and pyruvate⁻, and (3) d-betahydroxybutyrate⁻ and acetoacetate⁻.

Thus, one first optional class of solutions of this invention contains in addition to organic polyanionic material an inorganic class of anions comprised of chloride and bicarbonate. These solutions have a physiological pH which is broadly in the range from about 6.9 to 8.6, and more preferably in the range from about 7.35 to 7.45, and most preferably is about 7.4 (for human use). Dissolved carbon dioxide must also be present in these solutions with bicarbonate anions. When administered, these solutions not only tend to maintain a mammal's normal blood (and plasma) ratio of sodium to chloride, but also tend to set (regulate) the mammal's normal blood (plasma) pH at a normalized value.

Another second optional class (preferred) of such solutions characteristically contains a class of carboxylate anionic couple pairs comprised of at least one of (a) a mixture of D-betahydroxybutyrate anions and acetoacetate anions, and (b) a mixture of both (a) and (b). These solutions have a physiological pH which is as above defined in connection with such first optional class of solutions. When administered, these solutions not only tend to maintain the mammal's redox state within a normal range, but also tend to maintain that mammal's phosphorylation potential within a normal range.

Another (third) class (more preferred) of such solutions characteristically not only contains both chloride anions, and bicarbonate/carbon dioxide mixture, as in such (first) class of solutions, but also utilizes (contains) such class of carboxylate anionic couples, as in such (second) class of solutions. When administered, these solutions achieve the above indicated effects obtained from the use of such first optional class of solutions and the above indicated effects obtained from the use of such second optional class of solutions.

The total quantity, or sum (sigma), bicarbonate anions and carbon dioxide present in a solution of this invention ranges from 0 to about 465 millimoles per liter of solution, and preferably 0 to 55 millimoles/L. The ratio of bicarbonate milliequivalents per liter to dissolved carbon dioxide milliequivalents per liter in a solution of this invention can range from about 0.1/1 to 55/0.1 and preferably 11/1 to 24/1. More preferably, such total ranges from about 10 to 45 mM/l and such ratio ranges from about 18.1 to 26:1, and still more preferably, such total ranges from about 23 to 35 mM/l while such ratio ranges from about 19:1 to 21:1. A ratio of 19.95 for $[HCO_3^-]/[CO_2]$ gives a pH 7.4 which is presently particularly preferred.

The total quantity, or sum (sigma) of l-lactate anions and pyruvate anions present in a solution of this invention ranges from 0 to about 465 (preferably 0 to 55) millimoles per liter of solution. The ratio of l-lactate anion milliequivalents per liter to pyruvate anion milliequivalents per liter in a solution of this invention can range from about 20:1 to 1:1. Preferably, such total quantity ranges from about 0.5 to 10 mM/l and such ratio ranges from 3/1 to 15:1, and more preferably such total quantity ranges from about 2 to 8 mM/l while such ratio ranges from about 5:1 to 12:1.

The total quantity, or sum (sigma) of d-betahydroxybutyrate anions and acetoacetate anions present in a solution of this invention ranges from about 0 to about 465 (preferably 0 to 55) millimoles per liter of solution. The ratio of d-betahydroxybutyrate anion milliequivalents per liter to acetoacetate milliequivalents per liter in a solution of this invention can range from about 6:1 to 0.5:1. Preferably, such total ranges from about 1 to 10 mM/l and such ratio ranges from about 4:1 to 1:1, and more preferably such total ranges from about 2 to 8 mM/l while such ratio ranges from about 3:1 to 1.5:1.

One of the three near equilibrium couples optionally employed in the practice of this invention (the bicarbonate$^-$/carbon dioxide couple) tends, as used in this invention, to regulate the concentration of hydrogen ions in blood (plasma) and in the treated mammal's cells, and each one of such couples tends to normalize the redox state of each of the three pyridine nucelotide couples. The phosphorylation potential also tends to be normalized. Also, each such near equilibrium couple when used as herein described constitutes a safe entry point into the metabolic system of a mammal.

Further, each such near equilibrium couple, if utilized in this invention, exhibits a distribution between intracellular fluid and extracellular fluid such that the ratio of the concentrations in, respectively, intracellular fluid to extracellular fluid ranges from about 1:1 to 1.5:1 in most all mammalian cells.

One skilled in the art may wish to include with a polyanionate an aqueous electrolyte solution of this invention containing a total of not less than about 0.05 to 0.1 mM/l of at least one of such three near equilibrium couples and not more than about 465 mM/l thereof and preferably from 0 to 55 millimoles/liter.

The preferred cationic salt form of the polyanionate for purposes of plasma exspansion is the sodium form, however the other cations listed hereinbelow may be used. For the purposes of plasma exspansion pure $(Na^+)_z$ Polyanionate$^{z-}$ may be given as far superior to the uncharged materials currenetly used for the purpose of plasma exspansion. We prefer however to administer the material in a solution with the Na:Cl ratio in the range from 1.24 to 1.6.

Electrolyte Solutions

Electrolyte solutions of this invention which are presently preferred for physiologic usage are characterized as being comprised of water which has dissolved therein each of the following components in the amounts indicated:

TABLE V

| Component | | Quantity range mM/L preferred | broad |
|---|---|---|---|
| Total Cations | | 125–160 | 1–2400 |
| (1) | sodium$^+$ | 125–160 | 1–2400 |
| (2) | potassium$^+$ | 0–6 | 0–90 |
| (3) | calcium$^{2+}$ | 0–1.5 | 0–60 |
| (4) | magnesium$^{2+}$ | 0–1 | 0–15 |
| Total Anions | | 125–160 | 1–2400 |
| (5) | chloride$^-$ | 100–130 | 0–2000 |
| (6) | bicarbonate$^-$ | 0–55 | 0–465 |
| (7) | inorganic phosphate$^{z-}$ | 0–5 | 0–22 |
| (8) | l-lactate$^-$ + pyruvate$^-$ | 0–55 | 0–465 |
| (9) | d-β Hydroxybutyrate$^-$ + acetoacetate$^-$ | 0–55 | 0–465 |
| (10) | non diffusible polyanionate$^{z-}$ in mEq/L | 25–60 | 0.2–2400 |
| Total Nonionics | | 0–550 | 0–575 |
| (11) | carbon dioxide | 0–10 | 0–25 |
| (12) | osmotically active substance | 0–550 | 0–575 |

| the interrelationships between components being such that: | |
|---|---|
| mEq ratio of [bicarbonate]/[CO$_2$] | 1/1–55/0.1 |
| mEq ratio of [l-lactate$^-$]/[pyruvate$^-$] | 20/1–1/1 |
| mEq ratio of [d-hydroxybutyrate$^-$]/[acetoacetate$^-$] | 6/1–0.5/1 |
| mEq ratio of [Na$^+$]/[Cl$^-$]1.24–1.6[1] | 0–infinity |
| total of (6),(8),(9),(10) | 0.2–2400 |
| milliosmolarity | 260–5000 |
| pH | 5–9 |

[1]preferred

Preparation of polyanionic material

Any convenient preparative procedure may be used, for example:

Suitable Class II polyanionics are prepared as follows:

Albumin is taken in water (about 1.5 mM/l) and dialyzed for 48 hours against deionized water a 4 degrees C. It is treated with NaOH to a pH of 7.4 at which pH it has become about sodium$_{20}$ albuminate$^{-20}$.

Carboxymethyl starch prepared in sizes comparably to those available for Dextran (see Mudge GH. In: Gilman AG, Goodman LS, Gilman A. eds. *The Pharmacological Basis of Therapeutics*, 6th edition, Macmillan, New York, 1980, 859–862.) has a pK$_a$, of about 4 and can be prepared in the same manner as albumin. Likewise carboxymethyl dextrans are similarly prepared. Carboxymethylation can be conveniently accomplished, for example, by titration with chloroacetate. Any carboxy-lower alkyl groups may be used, but methyl is presently preferred.

Each of these products has a Z[conc$^{z-}$] term of about −14 mEq/l for use as a plasma substitute or plasma expander, for example, in the treatment of burns and war wounds, or as a counter polyanion in hemodialysis or peritoneal dialysis to cancel the need for adding toxic amounts of small organic anions such as d,l-lactate, acetate or chloride to such fluids to obtain a Na:Cl ratio of from 1.24 to 1.6.

Plasma Substitutes and Plasma Extenders

Electrolyte solutions of this invention containing non-diffusible polyanionics are useful as plasma substitutes and plasma extenders, and, in such usage, the presently most preferred non diffusible polyanionics are serum albumin and sodium albuminate, although other Class II polyanionics may be employed, such as carboxymethyl starch, poly gamma glutamate, and the like, preferably in the sodium form for human use.

Serum albumin is normally present in plasma at about 0.65 mM/l and at pH 7.4 has $-20$ charges per molecule for a Z[albumin concentration] term of about 13 to 14 mEq/L. From the relationship: $\pi = \Sigma[C]RT$ this osmotic pressure of serum albumin (which is $Na_{20}$ albuminate$^{20-}$) is about 264 mmHg. (Eqn 6.)

In contrast, the osmotic pressure for dextran (molecular weight 68,500 with no charge) is about 12.6 mmHg on the basis of Equation 6 above. For dextran to be equivalent to sodium albuminate in its osmotic effect, one would have to make the plasma contain about 13 mM/l dextran or about 90% solution. Such a solution would be so viscous as to be fatal in some circumstances. It is concluded that artificial plasma expanders must have net fixed negative charges at pH 7.2 to 7.4 and preferably be given in the sodium form to achieve the desired effect of expansion of the intravascular volume. It is further concluded that the currently described and widely used "ideal plasma expanders" (See Mudge in Goodman and Gilman 1980, cited above) are essentially worthless for the purposes for which they are currently used in medical practice.

Examples of non diffusible polyanionic materials useful in plasma substitutes and plasma extenders include albumin, sodium albuminate, carboxymethyl starch, any carboxy-lower alkyl starch, carboxymethyl cellulose, carboxymethyl dextrose, gamma polyglutamate, red cells, polyacrylamides, and polysulfonates. The sodium forms of these polyanionates are particularly preferred for the purpose of plasma volume expansion. Because of the higher charge density of the polysulfonates, this class is usable, but not preferred.

Utilization of Polyanionics

Polyanions of the type described have a particular application in the treatment of war wounds and burns, where stable preparations of effective plasma expanders are required. The use of these types of material in their Na-polyanionate form would be extremely effective and with lower toxicity than the current practice of using uncharged dextrans (See Williams TG, Riley TRD, Moody RA. *Brit Med J* 286: 775-777, 1983; Williams T. *Brit Med J* 296: 790-792, 1983). They may be used as a less toxic alternative to hypertonic (2400 mOsmolar) NaCl solutions in the treatment of hemorrhage (See Velasco IT et al *Am J Physiol* 239: H664-673, 1980, or to large volumes of crystaloid solutions such as Ringer's Lactate (See Nerlich M, Gunther R, Demling RH. *Circ Shock* 10: 179-188, 1983)

Insoluble, non diffusible polyanionics have a variety of uses, in filling the anion gap. They can be used in tissue culture medium or on the surface of tissue culture plates to create a suitable culture medium that carries a sodium (or cation) carboxylate such that the proper cationic composition can be obtained with a normal Na:Cl ratio.

Such polyanionic materials can also be used in dialysis fluids to obtain a desired Na:Cl ratio and to overcome the anion gap as an alternative to small anions, such as shown in my copending case, P-83, 2198 and P-85, 1402. Their large molecular size is such that they do not pass through the semipermeable membranes employed in hemodialysis.

A preferred class of solid insoluble non diffusible polyanionics comprises carboxy (lower alkyl) polymers. Examples include carboxylated styrene-divinylbenzene ion resins and acrylic ion exchange resins such as those available from such companies as Dow Chemical Company ("Dowex resins") and Rohm and Haas Company. The sulfonated resins may be used as anions, in, for example hemodialysis or on tissue culture plates to obtain the desired Na:Cl ratio, but should not be used intravascularly, where they may interfere with the clotting mechanism of blood (such as occurs with heparin).

Use of Polycationic Materials

Non diffusible polycationic materials can be used in accord with this invention to treat alkalosis and thus increase the sodium to chloride ratio without giving ammonia, which is undesirable because excessive ammonia administration: (1) causes what can be an excessive urea synthesis; (2) causes what can be major upsets in the cellular redox state and the cellular phosphorylation potential; and (3) can induce hepatic coma and death.

Determination of the Charge Value $|Z|$ [polyion$^{z+\ or\ -}$]

As follows from Eqn. 2, below, the number $Z \times$ [concentration of polyion] where Z is the absolute value of the net charge, $-$ or $+$/mole on polyionic substance, and [] indicates the molar concentration. From such values, the value $|Z|$ [polyion$^{z+\ or\ -}$] can be determined by placing the polyion in a dialysis sac through which it is impermeant and dialyzing it at equal pressure against an excess volume of diffusible salt solution, for example, NaCl, at any pH of interest. The ratios of $[Na^+]$ and $[Cl^-]$ in the dialyzing solution and inside the dialysis sac containing the polyion are related to the term $|Z|$ [polyion$^z$] according to Eqn 2 following:

$$[Na^+]_o/[Na^+]_i = [Cl^-]_i/[Cl^-]_o = [Cl^-]_o/\{[Cl^-]_i + |Z|[polyion^z]\}$$

EMBODIMENTS

The present invention is further illustrated by reference to the following examples. Those skilled in the art will appreciate that other and further embodiments are obvious and within the spirit and scope of this invention from the teachings of these present examples taken with the accompanying specification.

EXAMPLES 1-2

Illustrative electrolyte solutions of this invention are provided. Example 1 is a modified Krebs-Henseleit solution wherein the Na:Cl ratio is normalized with sodium albuminate. Example 2 is artificial plasma expander which is an alternative to a dextran containing expander. It has 20 times the osmotic pressure of dextran.

When either of these two solutions is used as a plasma expander for the treatment of a severely wounded man who is hemorrhaging, it is found that the patient's blood pressure returns to normal, and that the patient's effective blood osmotic pressure normalizes as does the distribution of water between intravascular and intracellular space. Administration of an equivalent molar amount of a presently used plasma expander such as dextran or hydroxyethylstarch (but no sodium albuminate) is found not to elevate the patient's blood pressure and not to maintain the osmotic pressure of the patient's blood plasma.

TABLE

Examples of New Polyanionate Solutions for Contacting Living Cells, Either I.V., Through Dialysis Membranes, or In Vitro.

| Units mmoles | Normal Plasma N.E.J.M. 283, 1285 | (1) Krebs' Albuminate | (2) Veech's Polyanionate |
|---|---|---|---|
| L fluid | 1970 | | |
| $Na^+$ | 136–145 | 138 | 142 |
| $K^+$ | 3.5–5.0 | 4.0 | 4.5 |
| $\Sigma Ca$ | 2.1–2.6 | 2.25 | 1.1 |
| free $[Ca2+]$ | [1.06] | | |
| $\Sigma Mg$ | 0.75–1.25 | 1.00 | 0.56 |
| free $[Mg2+]$ | [0.53] | | |
| $\Sigma$ mEq Cations | 142.7–153.2 | 148.5 | 149.73 |
| $Cl^-$ | 100–106 | 103 | 102 |
| $HCO_3^-$ | 26–28 | 29 | 29 |
| $\Sigma$ Pi | 1–1.45 | 1.2 | 1.1 |
| $SO_4^{2-}$ | 0.32–0.94 | — | — |
| L-lactate$^-$ | 0.6–1.8 | | |
| pyruvate$^-$ | | | |
| Lact/pyr | | | |
| D-$\beta$-OHbutyrate$^-$ | | | |
| acetoacetate$^-$ | | | |
| $\beta$-HB/ acac | | | |
| acetate$^-$ | | | |
| Other | | 0.73 mM Albuminate (−14.6 mEq) | 0.70 mM Carboxymethyl-Starch (−16.7 mEq) |
| $\Sigma$ mEq anions | 128.7–139.4 | 148.8 | 149.73 |
| $Na^+/Cl^-$ | 1.28–1.45 | 1.34 | 1.39 |
| Glucose or others | 3.9–5.6 | — | — |
| $CO_2$ | 0.99–1.39 | 1.54 | 1.54 |
| pH | 7.35–7.45 | 7.4 | 7.4 |
| $\Sigma$ mOsm | 285–295 | 280.7 | 307 |
| Use: | | (1) IV infusion | (1) Alternative to Dextran or Hydroxyethylstarch as a plasma expander. |
| | | (2) As dialysis fluid | (2) As dialysis fluid |
| | | (3) Tissue culture | (3) As tissue culture media |
| | | (4) Contacting living cells | (4) Contancting cells |

(1) Bovine serum albuminate is prepared as described and carries about 20 -/ mole. For human use, human albumin is used.
(2) A 70,000 MW starch, with a D-glucose primarily in a 1–4 linkage or alternatively with the a 1–6 linkage is prepared chloroacetate to give about 24 Na—carboxylate groups/mole.

The laws and relationships controlling the technology and the effects described therein are presented in the following equations. There is not intent to be bound by theory.

Various changes, improvements, alternatives, uses, and the like, will be apparent to those skilled in the art from the present description, and no undue limitations are to be inferred or implied.

0. Eqn 0 - The Second Law
J. Willard Gibbs. On the equilibrium of heterogeneous substances. J Conn Acad Sci 1876; III: 343.
0 - 1 Definition of Gibbs Free Energy and Other Properties of State:

$$G = H - TS$$

where:
$G \sim$ Gibbs free energy
$H \sim$ Enthalpy or heat content
$T \sim$ absolute temperature
$S \sim$ Entropy, or state of randomness or disorder 0 - 1a Entropy may be more rigorously defined by statistical and quantum mechanics in the Boltzmann Equation:

$$S = k_B \ln \Omega$$

where:
$S \sim$ Entropy
$k_B \sim$ Boltzmann constant $= \dfrac{R \text{ (gas constant)}}{\text{Avagadro's number}}$
$= 1.38 \times 10^{-23}$ J/°K.

$\Omega \sim$ Degeneracy

0 - 2 $\Delta G = \Delta H - T\Delta S$
where $\sim$ change in

0 - 3 Standard Free Energy $\sim \Delta G^o$ $$\Delta G = \Delta G^o + RT \ln \frac{[\text{products}]}{[\text{reactants}]}$$

where:
$R \sim$ gas constant
$= 1.987$ calories/°K./mole and °K. $\sim 273 + $ °C.
$T = $ °K.
$\ln \sim 2.303 \log_{10}$ 0 - 3a $\Delta G^o = -RT \ln K_{eq}$
where:

$$K_{eq} \sim \frac{[\text{products}]}{[\text{reactants}]}$$

0 - 4 At equlibrium, $\Delta G = 0$, so in $A + B \rightleftharpoons C + D$ $$\Delta G = -RT \ln K_{eq} + RT \ln \frac{[C][D]}{[A][B]}$$

where:
[ ] ~ activity or ~ concentration

"A theory is the more impressive the greater the simplicity of its premises, the more different are the kinds of things it relates, and the more extended is its range of applicability ... It is the only physical theory of universal content which I am convinced, that within the framework of applicability of its basic concepts, will never be overthrown."

A. Einstein

I Eqn 1 - The Henderson-Hasselbalch Equation

The major buffer and controller of extra- and intracellular pH.
Henderson LJ. Blood, A Study in General Physiology.
Silliman Lectures, Yale University Press, 1928

1.a
$$pH = pK_{a'} + \log \frac{[HCO_3^-]}{[CO_2]}$$

where:
$pK_{a'} = 6.10$ at 38° C. and serum concentrations of electrolytes 1.b The solubility of $CO_2$ in fluid, i.e. dissolved $CO_2$ gas plus $H_2CO_3$ from:

$$CO_2 + H_2O \rightleftharpoons H_2CO_3$$

$$[CO_2] \text{ in mmol/liter} = \frac{pCO_2 \text{ in mmHg}}{760 \text{ mmHg}} \cdot \frac{\alpha \text{ ml } CO_2/\text{ml of } H_2O}{22.26 \text{ L/mole}} \cdot \frac{1000 \text{ mmol}}{\text{mole}}$$

$\alpha_{CO_2} = 0.553/\text{ml serum } H_2O$ at 38° C. from:
Van Slyke DD. J Biol Chem 73: 765-799, 1928.

1.c The pH of a bicarbonate containing solution to which has been added a carbocylic acid such as acetic, lactic, acetoacetic acid with a pK' in the 3 to 4 range and where the concentration of $HCO_3$ is much larger that the concentration of carboxcylic acid:

$$pH = pK_{a'} - \log\left\{\frac{[HCO_3^-]}{2([HCO_3^-] - [HA])} - \frac{1}{2}\right\}$$

Thus adding 1.8 mM Hlactate and 0.2 mM Hpyruvate to 25 mM $NaHCO_3$ yields what pH?

$$pH = pK_{a'} - \log\left\{\frac{[25]}{2([HCO_3 - [HA])} - \frac{1}{2}\right\}$$

$= 6.1 - (1.36)$
$= 7.46$

II Donnan Equilibrium Equation

Donnan FG. Z Electrochem 17: 572, 1911
Donnan FG. Chem Rev 1: 73-90, 1924.

1. From Gibbs (Eqn 0)

$$RT \ln \frac{[Cl^-]_1}{[Cl^-]_2} + RT \ln \frac{[Na^+]_1}{[Na^+]_2} = 0$$

```
           ΔE
    1  ↘      ↗  2   ⎫ Δp
[Na⁺]₁        [Na⁺]₂  ⎬
[Cl⁻]₁  ↙  ↘  [Cl⁻]₂ ⎭
Z[A^z⁻]₁  ↙
```

[ ] ≃ activity ≃ concentration
$A$ ≃ non-diffusable polyanion
$Z$ ≃ valance of polyanion
Or:

1.a
$$\frac{[Cl^-]_1}{[Cl^-]_2} = \frac{[Na^+]_2}{[Na^+]_1}$$

Therefore: $\frac{[Cl^-]_1}{[Cl^-]_2} = \frac{[Cl^-]_2}{[Cl^-]_1 + Z[A^{z-}]_1} = \frac{[Na^+]_2}{[Na^+]_1}$ and for polyvalents:

$$\left\{\frac{[Anions]_1}{[Anions]_2}\right\}^{1/z \text{ anions}} = \left(\frac{[Cations]_2}{[Cations]_1}\right)^{1/z \text{ cations}}$$

2. From the Law of Electrically Neutrality:
$[Na^+]_2 = [Cl^-]_2$
$[Na^+]_1 = [Cl^-]_1 + Z[A^{z-}]_1$ 3. Quadratic equation:

$$x = \frac{-b + \sqrt{b^2 - 4ac}}{2a}$$

Example: Consider albumin dialysed against 100% $CO_2/3.13$ $NaHCO_3$ buffer with 1.17 mM albumin (i.e. 8% solution). Hypothetically keep charge on albumin at $-20/\text{mole}$.

$$\frac{[HCO_3^-]_i}{[HCO_3^-]_o} = \frac{[HCO_3^-]_o}{[HCO_3^-]_i + 20[Alb^{-20}]} = \frac{[Na^+]_o}{[Na^+]_i}$$

$$\frac{[HCO_3^-]_i}{[3.13 \times 10^{-3}]} = \frac{[3.13 \times 10^{-3}]}{[HCO_3^-]_i + 20[1.17 \times 10^{-3}]}$$

$[HCO_3^-]_i = 0.4 \times 10^{-3}M$

II Eqn 2 Multicomponent Donnan Equilibrium System for Solutions Such as the Hemodialysis of Blood Plasma Electrolytes:

where $\Delta p = 0$ and all components but albumin are permeant. Subscript $_o$ ~ in dialysis fluid, subscript $_i$ ~ in patient's plasma, $\Delta p$ ~ difference in pressure.

2.a.
$$\frac{[Na^+]_i}{[Na^+]_o} = \frac{[K^+]_i}{[K^+]_o} = \left\{\frac{[Ca^{2+}]_i}{[Ca^{2+}]_o}\right\}^{\frac{1}{2}} = \left(\frac{[Mg^{2+}]_i}{[Mg^{2+}]_o}\right)^{\frac{1}{2}} =$$

$$\frac{[Cl^-]_o}{[Cl^-]_i} = \frac{[HCO_3^-]_o}{[HCO_3^-]_i} = \left(\frac{[\Sigma Pi]_o}{[\Sigma Pi]_i}\right)^{1/1.8} = \frac{[lac^-]_o}{[lac^-]_i} =$$

$$\frac{[pyr^-]_o}{[pyr^-]_i} = \frac{[acac^-]_o}{[acac^-]_i} = \frac{[BHB^-]_o}{[BHB^-]_i} = \frac{[acet^-]_o}{[acet^-]_i}$$

Statement of electrical neutrality on two sides of an uncharged membrane 2.b.1. $[Na^+]_o + [K^+]_o + 2[Ca^{2+}]_o + 2[Mg^{2+}]_o = [Cl^-]_o + [HCO_3^-]_o + 1.8[\Sigma Pi^{-1.8}]_o + [lac^-]_o + [pyr^-]_o + [acac^-]_o + [BHB^-]_o + [acet^-]_o$ 2.b.2. $[Na^+]_i + [K^+]_i + 2[Ca^{2+}]_i + 2[Mg^{2+}]_i = [Cl^-]_i + [HCO_3^-]_i + 1.8[\Sigma Pi^{-1.8}]_i + [lac^-]_i + [pyr^-]_i + [acac^-]_i + [BHB^-]_i + [acet^-]_i + Z[prot^{z-}]_i$ Distribution of cations on two sides of the membrane:

2.c
$$[K^+]_i = [K^+]_o \frac{[Na^+]_i}{[Na^+]_o} \; ; \; [Ca^{2+}]_i = [Ca^{2+}]_o \left\{\frac{[Na^+]_i}{[Na^+]_o}\right\}^2 \; ;$$

$$[Mg^{2+}]_i = [Mg^{2+}]_o \left\{\frac{[Na^+]_i}{[Na^+]_o}\right\}^2$$

Distribution of Anions:

-continued 2.d $$[Cl^-]_i = \frac{[Na^+]_o}{[Na^+]_i}[Cl^-]_o; \quad [HCO_3^-]_i = \frac{[Na^+]_o}{[Na^+]_i}[HCO_3^-]_o;$$

$$[acet^-]_i = \frac{[Na^+]_o}{[Na^+]_i}[acet^-]_o; \quad [\Sigma Pi]_i = \left\{\frac{[Na^+]_o}{[Na^+]_i}\right\}^{1.8}[\Sigma Pi]_o;$$

$$[lac^-]_i = \frac{[Na^+]_o}{[Na^+]_i}[lac^-]_o; \quad [pyr^-]_i = \frac{[Na^+]_o}{[Na^+]_i}[pyr^-]_o;$$

$$[acac^-]_i = \frac{[Na^+]_o}{[Na^+]_i}[acac^-]_o; \quad [BHB^-]_i = \frac{[Na^+]_o}{[Na^+]_i}[BHB^-]_o$$

Now solving for $[Na^+]_i/[Na^+]_o$ for a dialysis fluid$_o$ of known composition:

2.e $$\frac{[Na^+]_i}{[Na^+]_o}\left\{[Na^+]_o + [K^+]_o + \frac{2[Na^+]_i}{[Na^+]_o}([Ca^{2+}]_o + [Mg^{2+}]_o)\right\} = \frac{[Na^+]_o}{[Na^+]_i}\left\{[Cl^-]_o + [HCO_3^-]_o + [acet^-]_o + [lact^-]_o + [pyr^-]_o + [acac^-]_o + [BHB^-]_o + 1.8\left(\frac{[Na^+]_o}{[Na^+]_i}\right)^{0.8}[\Sigma Pi]_o + \frac{[Na^+]_i}{[Na^+]_o}|Z|[prot^{z-}]\right\}$$

and:

2.f $$\frac{[Na^+]_o + [K^+]_o}{[Na^+]_o^2}[Na^+]_i^2 + \frac{2([Ca^{+2}]_o + [Mg^{2+}]_o)}{[Na^+]_o^3}[Na^+]_i^3 - |Z|\frac{[prot^{z-}]}{[Na^+]_o}[Na^+]_i - (1.8[\Sigma Pi]_o[Na^+]_o^{0.8})[Na^+]_i^{(-0.8)} =$$

-continued
$$[Cl^-]_o + [HCO_3^-]_o + [acet^-]_o + [lact^-]_o + [pyr^-]_o + [acac^-]_o + [BHB^-]_o$$

Plasma [concentration] ~ 0.935 × plasma H$_2$O [concentration]

III Eqn 3. Nernst Equation - $\Delta E$

Nernst W. Theoretical Chemistry 4th Edition, 1904, McMillan, London. See also Silliman Lecture, 1906, Yale U. Press, New Haven.

3. $$\Delta E = -\frac{RT}{nF}\ln\frac{[anion^-]outside}{[anion^-]inside}$$

or:

$$\Delta E = -\frac{RT}{nF}\ln\frac{[cation^+]inside}{[cation^+]outside}$$

where:
at 38° C. $T \sim 311°$ K.
$R$, the gas constant ~ 8.314 joules/degree/mole
$n$ ~ number of equivilents
F, the Faraday, ~ 96,494 coulombs
$\Delta E$ ~ potential in volts
To convert ln to log$_{10}$, multiply by 2.303
From Cornell N, Anal Biochem 1980; 102: 326–332, for isolated hepatocytes from starved rats incubated in Krebs-Henseleit.

$$\Delta E = -0.0617\log\frac{[0.128 \text{ M Cl}^-]outside}{[0.041 \text{ M Cl}^-]inside}$$

$\Delta E = -0.0305$ V or - 30.5 mV
and for cat brain, from Eccles JC. The Physiology of Nerve Cell, 1957, Johns Hopkins U Press, Baltimore.

$$\Delta E = -0.0617\log\frac{[0.125 \text{ M Cl}^-]outside}{[0.009 \text{ M Cl}^-]inside}$$

$\Delta E = -0.0705$ V or - 70.5 mV 3.b Redox Potential of Half Reactions $$E_n = E^o + \frac{RT}{nF}\ln\frac{[oxidized]}{[reduced]}$$

where:
$R \sim 8.31431$ J/°K./mole
$T \sim$ °K.
$n$ ~ number of electrons,
F ~ Faraday ~ 96,494 coulombs
ln ~ 2.303 log$_{10}$

IV Eqn 4 Redox State Equations. [NAD$^+$]/[NADH] or [NADP$^+$]/[NADPH].

Near equlibrium reactions are given a number depending upon location. The $E^{o'}$ of the [NAD$^+$]/[NADH] couple at pH 7 is $-0.32$ V. That of the [NADP$^+$]/[NADPH] couple, $-0.335$ V.

| Abbreviation Enzyme No. | Definition of $K_{eq}$ | Value of $K_{eq}$ at pH = 0 | Value of $K_{eq}$ at pH 7 | $E^{o'}$ at pH 7.0 oxidized/reduced V | $E^{o'}$ at pH 7.0 CO$_2$ = 1.5 mM or 0.5 mM NH$_4^+$ or 1 mM Pi V |
|---|---|---|---|---|---|
| | Cytoplasmic NAD - Linked Dehydrogenases | | | | |
| 4c1 | $K_{LDH} = \frac{[pyruvate^-][NADH][H^+]}{[1\text{-lactate-}][NAD^+]}$ EC 1.1.1.27 | $1.11 \times 10^{-11}$M | $1.11 \times 10^{-4}$ | $-0.201$ | |
| 4c2 | $K_{MDH} = \frac{[oxaloacetate^{2-}][NADH][H^+]}{[1\text{-malate}^{2-}][NAD^+]}$ EC 1.1.1.37 | $2.86 \times 10^{-12}$M | $2.86 \times 10^{-5}$ | $-0.184$ | |
| 4c3 | $K_{GPDH} = \frac{[\alpha\text{-glycerol-P}^{2-}][NADH][H^+]}{[DHAP^{2-}][NAD^+]}$ | $1.3 \times 10^{-11}$M | $1.3 \times 10^{-4}$ | $-0.203$ | |

-continued

EC 1.1.1.94

| | | | | | | |
|---|---|---|---|---|---|---|
| 4c4 | $K_{GAPDH} = \dfrac{[1,3\text{ DiPG}^{4-}][NADH][H^+]}{[GAP^{2-}][Pi^{2-}][NAD^+]}$ EC 1.2.1.12 | $5.3 \times 10^{-8}$M | $5.3 \times 10^{-1}$ | −0.302 | −0.222 | Here, Pi is a reactant |
| | $K_{ADH} = \dfrac{[\text{acetaldehyde}][NADH][H^+]}{[\text{ethanol}][NAD^+]}$ EC 1.1.1.1 | $1.94 \times 10^{-11}$M | $1.9 \times 10^{-4}$ | −0.209 | | |
| | $K_{IdDH} = \dfrac{[\text{d-fructose}][NADH][H^+]}{[\text{d-sorbitol}][NAD^+]}$ EC 1.1.1.14 | $1.14 \times 10^{-9}$M | $1.14 \times 10^{-2}$ | −0.262 | | |

Mitochondrial NAD - Linked Dehydrogenases

| | | | | | |
|---|---|---|---|---|---|
| 4m1 | $K_{HBDH} = \dfrac{[\text{acetoacetate}^-][NADH][H^+]}{[\text{d-}\beta\text{-hydroxybutyrate-}][NAD^+]}$ EC 1.1.1.30 | $4.93 \times 10^{-9}$M | $4.93 \times 10^{-2}$ | −0.281 | |
| 4m2 | $K_{GlDH} = \dfrac{[\alpha\text{-KG}^{2-}][NH_4^+][NADH][H^+]}{[\text{l-glutamate}][NAD^+]}$ EC 1.4.1.3 | $3.87 \times 10^{-13}$M$^2$ | $3.87 \times 10^{-6}$M | −0.158 | −0.257 |
| | $K_{AlDH} = \dfrac{[\text{acetate}^-][NADH][H^+]^2}{[\text{acetaldehyde}][NAD^+]}$ EC 1.2.1.3 | $1.45 \times 10^{-5}$M$^2$ | $1.45 \times 10^{+9}$ | −0.596 | |

Cytoplasmic NADP - Linked Dehydrogenases

| | | | | | |
|---|---|---|---|---|---|
| 4T1 | $K_{IcDH} = \dfrac{[\alpha\text{-KG}^{2-}][CO_2][NADPH]}{[l_s\text{-isocitrate}^{3-}][NADP^+]}$ EC 1.1.1.42 | 1.17M | 1.17M | −0.337 | −0.422 Here, $CO_2$ is a reactant |
| 4T2 | $K_{Malic\ Enz} = \dfrac{[\text{pyruvate}^-][CO_2][NADPH]}{[\text{malate}^{2-}][NADP^+]}$ EC 1.1.1.40 | $3.44 \times 10^{-2}$M | | | |
| 4T3 | $K_{6PGDH} = \dfrac{[\text{ribulose 5-P}^{2-}][CO_2][NADPH]}{[\text{6-phosphogluconate}^{3-}][NADP^+]}$ EC 1.1.1.43 | $1.72 \times 10^{-1}$M | | | |

Linking Isomerases

| | | |
|---|---|---|
| 4L1 | $K_{GOT} = \dfrac{[\alpha\text{-KG}^{2-}][\text{l-aspartate}^-]}{[\text{l-glutamate-}][\text{oxaloacetate-}]}$ EC 2.6.1.1 | 6.61 |
| 4L2 | $K_{GPT} = \dfrac{[\alpha\text{-KG}^{2-}][\text{l-alanine}]}{[\text{l-glutamate-}][\text{pyruvate-}]}$ EC 2.6.1.2 | 1.52 |
| 4L3 | $K_{TPI} = \dfrac{[\text{dihydroxyacetone-P}^{2-}]}{[\text{glyceraldehyde 3-P}^{2-}]}$ EC 5.3.1.1 | 22 |

References for Values of Near-Equlibrium Reactions in Equation 4

| Equation | Abbreviation | Reference |
|---|---|---|
| 4C1 | $K_{LDH}$ | Williamson DH, Lund P, Krebs HA. Biochem J 103: 514–527, 1967 |
| 4C2 | $K_{MDH}$ | Guynn R, Gelberg H, Veech RL. J Biol Chem 248: 6957–6965, 1973 |
| 4C3 | $K_{GPDH}$ | Russman W. Thesis, Munich, 1969. |
| 4C4 | $K_{GAPDH}$ | Cornell N, Leadbetter M, Veech RL. J Biol Chem 254: 6522–6527, 1979 |
| 4M1 | $K_{HBDH}$ | Williamson DH, Lund P, Krebs HA. Biochem J 103: 514–527, 1967 |
| 4M2 | $K_{GLDH}$ | Engel P, Dalziel K. Biochem J 105: 691–695, 1967 |
| 4T1 | $K_{IcDH}$ | Londesbourgh J, Dalziel K. Biochem J 110: 217–222, 1968 |
| 4T2 | $K_{M.E.}$ | Veech R, Eggleston LV, Krebs HA. Biochem J 115: 609–619, 1967 |
| 4T3 | $K_{6PGDH}$ | Villet R, Dalziel K. Biochem J 115: 633–638, 1969 |
| 4L1 | $K_{GOT}$ | Krebs HA. Adv Enz Reg 13: 449–472, 1975 |
| 4L2 | $K_{GPT}$ | Krebs HA. Adv Enz Reg 13: 449–472, 1975 |
| 4L3 | $K_{TPI}$ | Veech RL, Raijman L, Dalziel K, Krebs HA. Biochem J 115: 837–842, 1969 |

*The enzyme aldose reductase EC 1.1.1.21 may be redox active during fructose infusion in certain tissues. The reaction is:

$$K_{Aldose\ R} = \frac{[\text{d-sorbitol}][\text{NADPH}][H^+]}{[\text{d-glucose}][\text{NADP}^+]} \sim 2 \times 10^{-11}M.* \text{ My estimate}$$

For description, see Hayman S, Kinoshita JH. J Biol Chem 240: 877, 1965

V Eqn 5 Phosphorylation State Equations - $[\Sigma ATP]/[\Sigma ADP][\Sigma Pi]$ Veech RL, Lawson JR, Cornell NW, Krebs HA. J Biol Chem 254: 6538–6547, 1979

5a. The equilibrium constant of the glyceraldehyde 3-phosphate dehydrogenase (EC 1.1.1.29) and 3 phosphoglycerate kinase reactions (EC 2.7.2.3) at 38° C., I = 0.25, and free $[Mg^{2+}]$ = 1 mM is:

$$K_{G+G} = \frac{[\Sigma 3PG]}{[\Sigma GAP]} \cdot \frac{[\Sigma ATP]}{[\Sigma ADP][\Sigma Pi]} \cdot$$

$$\frac{[NADH][H^+]}{[NAD^+]} = 1.83 \times 10^{-4}$$

5b. Combining the above reaction with $K_{LDH}$ and substituting [DHAP] = [GAP]/22

$$\frac{K_{G+G}}{K_{LDH}} = \frac{[\Sigma 3PG]}{[\Sigma GAP]} \cdot \frac{[\Sigma ATP]}{[\Sigma ADP][\Sigma Pi]} \cdot$$

$$\frac{[1\text{-lactate}]}{[\text{pyruvate}]} = 1.65 \times 10^{+7} M^{-1}$$

5c. Or:

$$\text{Free Cytoplasmic } \frac{[\Sigma ATP]}{[\Sigma ADP][\Sigma Pi]} = \frac{[\Sigma DHAP]}{[\Sigma 3PG]} \cdot$$

$$\frac{[\text{pyruvate}]}{[1\text{-lactate}]} \times 7.5 \times 10^{+5} M^{-1}$$

5d. Alternatively, from the creatine phosphokinase reaction (EC 2.7.3.2)

$$K_{CK} = \frac{[\Sigma ATP]}{[\Sigma ADP]} \cdot$$

$$\frac{[\text{creatine}]}{[\Sigma \text{creatine-P}][H^+]} = 1.66 \times 10^{-9} M^{-1}$$

For the Pyrophosphorylation State or $[\Sigma PPi]/[\Sigma Pi]$:
Lawson JWR, Guynn RW, Cornell NW, Veech RL,
In Gluconeogenisis (Hanson RW, Mehlman MA eds)
pp 481–511, John Wiley, New York, 1976

5e. From the UDPG Pyrophosphorylase reaction (EC 2.7.7.9):

$$\text{Free Cytoplasmic } [\Sigma PPi] = \frac{[\Sigma \text{glucose 1-P}][\Sigma UTP]}{[\Sigma UDPglucose] K_{UDPGPPiase}}$$

where $K_{UDPGPPiase}$ = 4.55

5f. For liver and blood glucose:

$$K_{G\text{-}PPi\ Trans\ Pase} = \frac{[\Sigma \text{Glucose 6-P}][\Sigma Pi]}{[\text{Glucose}][PPi]} = 45.9$$

5g.
$$K_{G6\text{-}P\text{-}PPi\ Trans\ Pase} = \frac{[\text{free F 1,6 diP}][\Sigma Pi]}{[\Sigma \text{fructose 6-P}][\Sigma PPi]} = 29.0$$

VI Eqn 6 Determination of Osmotic Pressure - $\pi$

Van't Hoff JH. Arch Neerl Sci 20: 239–303, 1886

$\pi = \Sigma[C] RT$ where:
$\pi \sim$ osmotic pressure in atmospheres (relative to pure $H_2O$)
$\Sigma[C] \sim \Sigma$[concentrations] of solutes in mole/liter
$R \sim$ gas constant = 0.082 liter atmospheres/mole/degree K.
$T \sim 273 +$ °C.

VII Eqn 7 The Equation of State of the Cell

Relating the $\Delta E$ across the cell membrane, the distribution of $[Na^+]$, $[K^+]$, $[Cl^-]$, and $[Ca^{2+}]$ between extracellular fluid and cytoplasmic $H_2O$ and hence cell volume to the cytoplasmic $[\Sigma ATP]/[\Sigma ADP][\Sigma Pi]$ $$\Delta G_{NA/K\ ATPase} = \Delta G^0_{ATPase} + \Delta G^0_{ions} + RT \ln \frac{[\Sigma ADP][\Sigma Pi]}{[\Sigma ATP]} +$$

$$RT \ln \frac{[Na^+]_o^3[K^+]_i^2[Cl^-]_o}{[Na^+]_i^3[K^+]_o^2[Cl^-]_i} + T\Delta S$$

Since $\Delta G = 0$, then:
$0 = -7.73$ kcal/mole $+ 0 + (-6.3$ kcal/mole$) +$
$8.5$ kcal/mole $+ 5.5$ kcal/mole As 1 kcal/mole $= \frac{0.082 \text{ liter atmos/mole/}°K.}{1.98 \times 10^{-3} \text{ kcal/mole/}°K.} \times$ $$\frac{1}{22.4 \text{ l/mole}} = 1.85 \text{ atmospheres}$$

then the $T\Delta S$ term $= 5.5 \times 1.85 = 10.2$ atmospheres.
And further from Van't Hoff (Eqn 6)

$$\Sigma[C]_{in} - \Sigma[C]_{out} = \frac{\pi}{RT}$$

$\Sigma[C]_{in} - \Sigma[C]_{out} = 0.40$ moles/L

Eqn 7 states that since $U_{T\ H_2O}$ outside $= U_{T\ H_2O}$ inside, the cell is prevented from swelling by the $Na^+/K^+$ ATPase which electroneutrally pumps out 2 mOsmoles/ATP hydrolysed. The $\Delta E$ across the cell (membrane) is reflected by the distribution of $[Cl^-]_o/[Cl^-]_i$ in accordance with the Nernst equation (Eqn 3). The $T\Delta S$ or decreased entropy within the living cell represents the increase "order" characteristic of the living cell. See Eqn 0. 7b. From the high capacity $Na^+/Ca^{2+}$ exchanger written in an electroneutral manner reflecting the free permeability of $Cl^-$ in accordance with the dictates of the Nernst equation, (Eqn 3):

$$3 Na^+_o + Ca^{2+}_i + Cl^-_o \rightleftharpoons 3 Na^+_i + Ca^{2+}_o + Cl^-_i$$

The net osmolar movement of eqn 7a is 2 osmoles $\rightarrow$ outside.
In contrast, the net movement of eqn 7b is 3 osmoles $\rightarrow$ inside, requiring the $Na^+/K^+$ ATPase to cycle 3 times for each 2 times the $Na^+/Ca^{2+}$ exchange mechanism operates in order to maintain osmotic equilibrium.
The gradient $[Ca^{2+}]_i/[Ca^{2+}]_o$ is thus a direct function of the $[Na^+]_o^3/[Na^+]_i^3$, (the $[Cl^-]_o/[Cl^-]_i$), and a function of the phosphorylation and entropy state of the cell.

Although the teachings of my invention have been herein disclosed with reference to certain embodiments and illustrations, it is to be understood that such are by way of illustration only and that others may wish to utilize my invention in different designs, applications, or the like.

I claim:

1. An aqueous electrolyte solution comprising water having dissolved therein:
   (a) at least one inorganic cation or at least one inorganic anion,
   (b) at least one non diffusible synthetic organic polyionic material selected from the group consisting of polyanionic materials, polycationic materials, and mixed polyanionic/polycationic materials provided that:

(1) the concentration of any one of (a), and (b) always ranges from about 0.1 to 5,000 millimoles per liter, (2) the total positive charges equal the total negative charges, (3) the charge associated with a molecule of said polyionic material ranges from greater than 0 to infinity and (4) wherein the molarity thereof multiplied by the charge associated with a molecule thereof produces a total anionic equivalent equal to the apparent anion gap of such solution and makes up the apparent deficiency caused by said apparent anion gap.

2. An electrolyte solution, for contacting living animal cells comprising water which has dissolved therein the following components in the respective amounts indicated:

TABLE

| Component | | Quantity range mM/L |
|---|---|---|
| Total Cations | | 1–2400 |
| (1) sodium$^+$ | about | 1–2400 |
| (2) potassium$^+$ | about | 0–90 |
| (3) calcium$^{2+}$ | about | 0–60 |
| (4) magnesium$^{2+}$ | about | 0–15 |
| Total Anions | about | 1–2400 |
| (5) chloride$^-$ | about | 0–2000 |
| (6) bicarbonate$^-$ | about | 0–465 |
| (7) inorganic phosphate$^{z-}$ | about | 0–22 |
| (8) l-lactate$^-$ + pyruvate$^-$ | about | 0–465 |
| (9) d-$\beta$ Hydroxybutyrate$^-$ + acetoacetate$^-$ | | 0–465 |
| (10) non diffusible synthetic organic polyanionate$^{z-}$ in mEq/L | | 0.2–2400 |
| and wherein the molarity thereof multiplied by the charge associated with a molecule thereof produces a total anionic equivalent equal to the apparent anion gap of such solution and makes up the apparent deficiency caused by said apparent anion gap | | |
| Total Nonionics | about | 0–575 |
| (11) carbon dioxide | about | 0–25 |
| (12) osmotically active substance | about | 0–550 |
| the interrelationships between components range from about: | | |
| mEq ratio of [bicarbonate$^-$]/[CO$_2$] | | 0.1/1–55/0.1 |
| mEq ratio of [l-lactate$^-$]/[pyruvate$^-$] | | 20/1–1/1 |
| mEq ratio of [d-hydroxybutyrate$^-$]/[acetoacetate$^-$] | | 6/1–0.5/1 |
| total of (6),(8),(9),(10) | | 0.2–465 |
| milliosmolarity | | 260–5000 |
| pH | | 5–9 |

3. The solution of claim 2 containing additionally about 20 to 44 percent by volume of red blood cells.

4. The solution of claim 2 wherein said non-diffusible polyanionic material is selected from the group consisting of albuminate, carboxymethyl starch, carboxy methyl, cellulose, carboxy methyl dextran, gamma polyglutamate, polyacrylamides, and polysulfonates.

5. The solution of claim 2 wherein said non-diffusible polyanionic material contains pendant acidic groups.

6. In an aqueous solution of the physiological type containing inorganic cations and inorganic anions in the respective amounts approximating those present in living animals, and wherein the apparent anion gap existing between total inorganic anions and total inorganic cations is provided by at least one organic anion, the improvement which comprises employing as such organic anion at least the non-diffusible synthetic organic polyanionic material wherein the molarity thereof multiplied by the charge associated with a molecule thereof produces a total anionic equivalent equal to the apparent anion gap of such solution and makes up the apparent deficiency caused by said apparent anion gap.

7. The solution of claim 6 wherein said polyanionic material comprises sodium albuminate.

8. The solution of claim 6 wherein said organic polyanionic material is selected from the group consisting of albuminate, carboxymethyl starch, carboxy-lower alkyl starch, carboxymethyl cellulose, carboxymethyl dextrose, gamma polyglutamate, polyacrylamides, and polysulfonates.

9. The solution of claim 6 wherein said solution is further characterized by having:

(A) sufficient total substances dissolved therein in the absence of any nonionics to produce an osmolarity ranging from about 260 to 5000 mOs, (B) the relationship between total ionic substances is such that the pH ranges from about 5 to 9, (C) charges of all cations equal charges of all anions, (D) at least one near equilibrium anionic couple is present additionally at a total concentration ranging from about 0.1 to 465 mM/L, each said couple being selected from the group consisting of (a) bicarbonate and carbon dioxide, (b) l-lactate and pyruvate, and (c) d-betahydroxybutyrate and acetoacetate.

10. An aqueous solution of plasma expansion comprising from about 1–2400 millimoles per liter sodium, from about 0.2 to 2400 milliequivalents per liter of at least one non-diffusible polyanionate having a net anionic charge ranging from about $-2$ to $-1000$ milliequivalents per millimole selected from the group consisting of albuminate, carboxymethyl starch, carboxyethyl starch, poly-d-betahydroxybutyrate, and carboxymethyl cellulose, and sufficient additional anions to achieve electrical neutrality selected from the anion group consisting of bicarbonate, inorganic phosphate, l-lactate, pyruvate, d-betahydroxybutyrate, and acetoacetate and the molarity of the polyanionate multiplied by the charge associated with a molecule thereof produces a total anionic equivalent equal to the apparent anion gap of such solution and makes up the apparent deficiency caused by said apparent anion gap.

11. The solution of claim 10 additionally containing from 0 to about 465 millimoles per liter of at least one of the following near equilibrium couples in the respective ratios indicated:

(A) bicarbonate and dissolved carbon dioxide, the bicarbonate to carbon dioxide ratio being about 0.1:1 to 55:1, (B) l-lactate and pyruvate, the l-lactate to pyruvate ratio being about 20:1 to 1:1, or (C) d-betahydroxybutyrate and acetoacetate, the d-betahydroxybutyrate to acetoacetate ratio being about 6:1 to 0.5:1.

12. An aqueous solution for plasma expansion comprising:

from about 125 to 160 millimoles per liter sodium, from about 100 to 130 millimoles per liter chloride, sufficient chloride to achieve a sodium to chloride milliequivalent ratio of from about 1.24:1 to 1.6:1, and from about 25 to 60 milliequivalents per liter of at least one polyanionic synthetic polymeric substance having a net anionic charge ranging from about −2 to −1000 milliequivalents/millimole selected from the group consisting of albuminate, carboxymethyl starch, carboxyethyl starch, poly-d-betahydroxybutrate, and carboxymethyl cellulose, and wherein the molarity thereof multiplied by the charge associated with a molecule thereof produces a total anionic equivalent equal to the apparent anion gap of such solution and makes up the apparent deficiency caused by said apparent anion gap having an pH ranging from about 5 to 9, and further having sufficient dissolved total osmotic material to produce an osmolarity ranging from about 260 to 5000 milliosmoles per liter.

* * * * *